United States Patent
Fujiyama et al.

(10) Patent No.: US 10,301,586 B2
(45) Date of Patent: May 28, 2019

(54) CELL CULTURING DEVICE, CELL CULTURING SYSTEM AND CELL CULTURING METHOD

(71) Applicants: SHIMADZU CORPORATION, Kyoto-shi, Kyoto (JP); TOKYO INSTITUTE OF TECHNOLOGY, Tokyo (JP)

(72) Inventors: Yoichi Fujiyama, Kyoto (JP); Yoh-ichi Tagawa, Tokyo (JP)

(73) Assignees: SHIMADZU CORPORATION, Kyoto-shi (JP); TOKYO INSTITUTE OF TECHNOLOGY, Tokyo (JP)

( * ) Notice: Subject to any disclaimer, the term of this patent is extended or adjusted under 35 U.S.C. 154(b) by 0 days.

(21) Appl. No.: 15/302,707

(22) PCT Filed: Apr. 14, 2014

(86) PCT No.: PCT/JP2014/060572
§ 371 (c)(1),
(2) Date: Oct. 7, 2016

(87) PCT Pub. No.: WO2015/159333
PCT Pub. Date: Oct. 22, 2015

(65) Prior Publication Data
US 2017/0029759 A1 Feb. 2, 2017

(51) Int. Cl.
*C12M 1/00* (2006.01)
*C12M 1/12* (2006.01)
(Continued)

(52) U.S. Cl.
CPC ............ *C12M 29/04* (2013.01); *C12M 23/34* (2013.01); *C12M 25/14* (2013.01); *C12M 29/00* (2013.01);
(Continued)

(58) Field of Classification Search
CPC ...... C12M 29/04; C12M 29/00; C12M 35/08; C12M 23/34; C12M 25/14; C12N 5/069; C12N 2502/14
See application file for complete search history.

(56) References Cited

U.S. PATENT DOCUMENTS 5,190,878 A 3/1993 Wilhelm
2003/0215941 A1 11/2003 Campbell et al.
(Continued)

FOREIGN PATENT DOCUMENTS

CN 202658162 U 1/2013
CN 202849409 U 4/2013
(Continued)

OTHER PUBLICATIONS

Machine Translation of WO 2012/032646 A1 (Year: 2018).*
Office Action dated May 30, 2017, issued in counterpart Japanese Application No. 2016-513504, with English machine translation. (6 pages).
(Continued)

*Primary Examiner* — Michael L Hobbs
(74) *Attorney, Agent, or Firm* — Westerman, Hattori, Daniels & Adrian, LLP

(57) ABSTRACT

A cell culturing device has: a first culture chamber; a first introduction flow channel and a first discharge flow channel which are connected to the first culture chamber; a second culture chamber connected to a halfway part of the first introduction flow channel via a first porous membrane; and a second introduction flow channel and a second discharge flow channel which are connected to the second culture chamber. The first discharge flow channel is connected to the first culture chamber via a second porous membrane. The first introduction flow channel has a liquid collecting part between the first culture chamber and the second culture chamber.

17 Claims, 10 Drawing Sheets

(51) Int. Cl.
*C12N 5/071* (2010.01)
*C12M 1/42* (2006.01)

(52) U.S. Cl.
CPC ............ *C12M 35/08* (2013.01); *C12N 5/069* (2013.01); *C12N 2502/14* (2013.01)

(56) References Cited

U.S. PATENT DOCUMENTS

| | | | |
|---|---|---|---|
| 2006/0263873 A1* | 11/2006 | Levine .................. | B01D 61/18 435/287.2 |
| 2007/0231887 A1 | 10/2007 | McGrath et al. | |
| 2012/0129257 A1* | 5/2012 | Yu ......................... | C12M 23/44 435/395 |

FOREIGN PATENT DOCUMENTS

| | | | | |
|---|---|---|---|---|
| JP | 11-75821 | A | | 3/1999 |
| JP | 2011-244713 | A | | 12/2011 |
| JP | 2013-165662 | A | | 8/2013 |
| WO | 2007/106868 | A2 | | 9/2007 |
| WO | 2012/032646 | A1 | | 3/2012 |
| WO | WO-2012032464 | A1 | * | 3/2012 ............. H04Q 1/142 |

OTHER PUBLICATIONS

Office Action dated May 3, 2017, issued in counterpart Chinese Patent Application No. 201480076730.8, with English translation. (13 pages).
Mazzei et al., "A Low Shear Stress Modular Bioreactor for Connected Cell Culture Under High Flow Rates", Biotechnol. Bioeng., vol. 106, No. 1, pp. 127-137, 2010.
Vozzi et al., "Connected Culture of Murine Hepatocytes and Human Umbilical Vein Endothelial Cells in a Multicompartmental Bioreactor", Tissue Eng. Part A, vol. 15, No. 6, pp. 1291-1299, Fig. 1, 2009.
Guzzardi et al., "Study of the Crosstalk Between Hepatocytes and Endothelial Cells Using a Novel Multicomparmental Bioreactor: A Comparison Between Connected Cultures and Cocultures", Tissue Eng. Part A, vol. 15, No. 11, pp. 3635-3644, 2009, Fig. 1.
Akechi et al., "Development of Liver-functional Devices", Shimadzu Review, vol. 67, No. 1-2, pp. 53-59, 2010.
International Search Report dated Jul. 22, 2014, issued in counterpart International Application No. PCT/JP2014/060572 (2 pages).
Office Action dated Aug. 28, 2017, issued in counterpart Chinese Application No. 201480076730.8, with English machine translation. (15 pages).
Decision of Rejection dated Feb. 27, 2018, issued in counterpart Chinese Application No. 201480076730.8 with English translation. (13 pages).

* cited by examiner

CELL CULTURING DEVICE, CELL CULTURING SYSTEM AND CELL CULTURING METHOD

TECHNICAL FIELD

The present invention relates to a cell culturing device, a cell culturing system and a cell culturing method.

BACKGROUND ART

Many studies on an artificial liver and the like have been conducted. However, cell culture of only a hepatic parenchymal cell for a long period of time has not been realized. The present inventors have reported that high liver functions are expressed by using a co-culture system of an endothelial cell and a hepatic parenchymal cell which forms a structured network due to the selection of a scaffold material, in the short term (see Non-Patent Document 1). A structure of a device suited for this system is disclosed, for example, in Patent Document 1.

PRIOR ART DOCUMENTS

Patent Document

Patent Document 1: Japanese Patent Laid-open Publication No. 2011-244713

Non-Patent Document

Non-Patent Document 1: Yoichi Fujiyama, Yoh-ichi Tagawa, and 5 other persons, "Analysis of liver functions in a co-culture with a hepatic parenchymal cell by using a system for culturing tubular endothelial liver cells", Proceedings of The 30th Annual Meeting of The Molecular Biology Society of Japan, 2007.

SUMMARY OF THE INVENTION

Problems to be Solved by the Invention

In the evaluation of pharmacokinetics, various methods have been studied in order to utilize an evaluation in a liver which use a co-culture system have also been developed.

However, a drug is not always directly incorporated into the liver in vivo, and therefore, it is preferable to consider the influence of the absorption of an ingredient in an intestine in the case of oral administration.

An object of the present invention is to provide a cell culturing device which is capable of culturing two types of cells and is capable of introducing a metabolite of one type of cells into the other type of cells, as well as a cell culturing system and a cell culturing method which utilize the cell culturing device.

Solutions to the Problems

The cell culturing device according to the present invention has a first culture chamber; a first introduction flow channel and a first discharge flow channel which are connected to the first culture chamber; a second culture chamber which is connected to a halfway part of the first introduction flow channel via a first porous membrane; and a second introduction flow channel and a second discharge flow channel which are connected to the second culture chamber.

The cell culturing system according to the present invention has: the cell culturing device according to the present invention; and a culture medium feeding part which feeds a culture medium into the first culture chamber by connecting a pump to the cell culturing device.

The cell culturing method according to the present invention has the steps of: culturing cells in the first culture chamber and in the second culture chamber, respectively, by using the cell culturing device according to the present invention; and introducing a liquid in the second culture chamber into the first culture chamber via the first porous membrane and the first introduction flow channel.

Effects of the Invention

The cell culturing device, the cell culturing system and the cell culturing method according to the present invention are capable of culturing two types of cells and are capable of introducing a metabolize of one type of cells to the other type of cells.

EMBODIMENTS OF THE INVENTION

Figure 1:
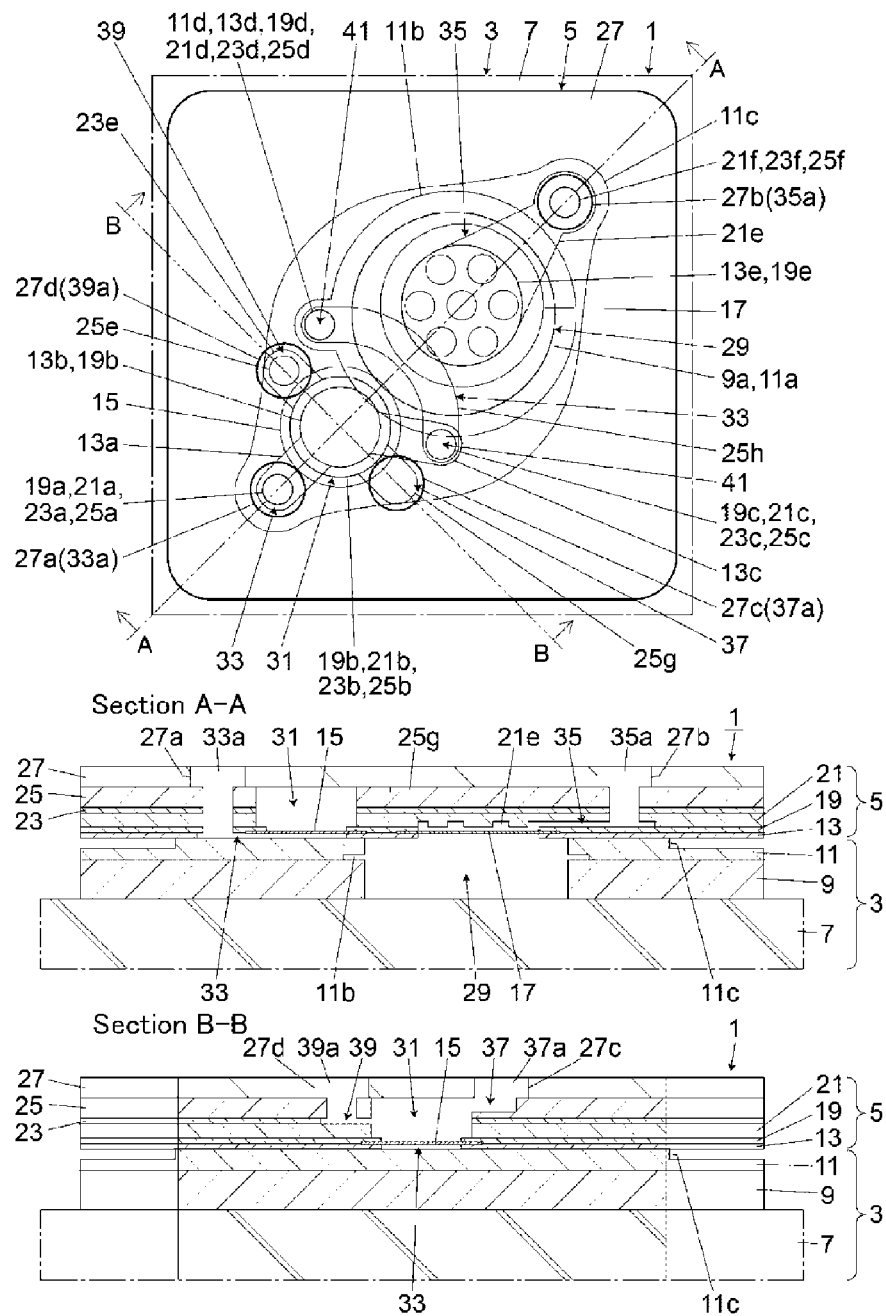
FIG. 1 is a schematic plan view and a cross-sectional schematic diagram for illustrating an example of a cell culturing device.

An example of the cell culturing device according to the present invention includes a cell culturing device in which the first discharge flow channel is connected to the first culture chamber via a second porous membrane. By this, for example, the clogging of the first discharge flow channel due to the influx of a substance in the first culture chamber such as a cell and a scaffold material (a gel) into the first discharge flow channel can be prevented. However, it is not necessary to arrange the second porous membrane in the cell culturing device according to the present invention.

An example of the cell culturing device according to the present invention includes a cell culturing device, in which the first introduction flow channel has a liquid collecting part between the first culture chamber and the second culture chamber, and in which at least a part of the wall of the liquid collecting part is formed by an elastic member which is capable of being penetrated by a suction implement having a sharp tip, wherein the through hole capable of being closed when the suction implement is withdrawn after the penetration due to the elasticity of the member. By this, a liquid which has passed through the second culture chamber, for example, a liquid which contains a metabolite of cells cultured in the second culture chamber, can be collected before the liquid is introduced into the first culture chamber. However, it is not necessary for the first introduction flow channel to have the liquid collecting part, in the cell culturing device according to the present invention.

An example of the cell culturing device according to the present invention includes a cell culturing device which has a main body and a lid part which is detachably attached to the main body part, in which the first culture chamber is formed in the main body, and has an opening on the surface of the main body part which is in contact with the lid part. By this, in a state where the main body part and the lid part are separated, for example, a substance such as a cell, a scaffold material and a culture medium can be placed in the first culture chamber without interposing the first introduction flow channel and the first discharge flow channel. However, the cell culturing device according to the present invention may have a structure which does not have the detachable main body part or the lid part.

In addition, an example of the cell culturing device includes a cell culturing device in which the material of a contact surface between the main body part and the lid part is a PDMS (polydimethylsiloxane) or a silicone rubber. By this, the lid part can be stably fixed to the main body part due to the self-adsorption property, for example, without using a special fixing means such as a screw and an adhesive agent. In addition, the main body part can be easily attached/detached to/from the lid part, as needed. However, the material of a contact surface between the main body part and the lid part is not limited to a PDMS or a silicone rubber, and materials other than the PDMS and the silicone rubber may be employed.

Further, an example of the cell culturing device includes a cell culturing device, in which at least one of the surface of the main body part in contact with the lid part and the surface of the lid part in contact with the main body part is formed in a convex shape, in which the plane size of the contact surface between the main body part and the lid part is smaller than the plane size of the device. By making the plane size of the contact surface between the main body part and the lid part smaller, a force distribution to an unnecessary part can be suppressed, and therefore, the adherence between the main body part and the lid part can be improved. However, both the surface of the main body part in contact with the lid part and the surface of the lid part in contact with the main body part may be flat surfaces, in the cell culturing device according to the present invention.

Furthermore, an example of the cell culturing device includes a cell culturing device in which the second culture chamber is formed in the lid part. By this, cells can be cultured in the first culture chamber and in the second culture chamber, respectively, under conditions and environments different from each other, by separating the main body part in which the first culture chamber is formed and the lid part in which the second culture chamber is formed. However, the second culture chamber may be formed in the main body part, or the second culture chamber may also be formed to be astride the main body part and the lid part, in the cell culturing device according to the present invention.

An example of the cell culturing device according to the present includes a cell culturing device, in which a co-culture system containing at least an endothelial cell and a hepatic parenchymal cell is co-cultured in the first culture chamber, and in which a cell derived from an intestine is cultured in the second culture chamber. By this, a metabolite of the cell derived from the intestine can be fed to the co-culture system which contains the endothelial cell and the hepatic parenchymal cell, and therefore, an environment closer to in vivo can be realized. However, the cell cultured in the first culture chamber and that cultured in the second culture chamber are not limited to these cells, in the cell culturing device according to the present invention.

In addition, an example of the cell culturing device according to the present invention includes a cell culturing device, in which a gel which serves as a cell scaffold material is housed in the first culture chamber, and in which the co-culture system having a tubular structure forms a structured network on the gel.

An example of the cell culturing system according to the present invention includes a cell culturing system, in which the culture medium feeding part feeds the culture medium to the first culture chamber by circulating the culture medium, and in which the cell culturing system further has a dialysis part in a halfway part of the culture medium circulating line of the culture medium feeding part. By this, the culture medium can be fed into the first culture chamber in a circulated manner while removing unnecessary substances by the dialysis part. This constitution is particularly useful in the case where a co-culture system, which contains at least an endothelial cell and a hepatic parenchymal cell, is co-cultured in the first culture chamber as well as a cell derived from an intestine is cultured in the second culture chamber. However, it is not necessary for the cell culturing system according to the present invention to have the dialysis part.

An example of the cell culturing method according to the present invention includes a cell culturing method, in which cells are cultured in the main part of the first culture chamber and in the second culture chamber which is formed in the lid part, respectively, in a state where the main body part and the lid part are separated from each other, by using the cell culturing device according to the present invention in which the second culture chamber is formed in the lid part, and thereafter, the main body part and the lid part are joined together. By this, cells can be cultured in the first culture chamber and in the second culture chamber, respectively, under conditions and environments different from each other. However, in the cell culturing method according to the present invention, cells may be cultured in the first culture chamber and in the second culture chamber, respectively, in a state where the main body part and the lid part of the cell culturing device are joined together.

An example of the cell culturing method according to the present invention includes a cell culturing method, in which a co-culture system containing at least an endothelial cell and a hepatic parenchymal cell is co-cultured in the first culture chamber, and in which a cell derived from an intestine is cultured in the second culture chamber. By this, a metabolite of the cell derived from the intestine can be fed to the co-culture system which contains the endothelial cell and the hepatic parenchymal cell, and therefore, an environment closer to in vivo can be realized. However, the cell cultured in the first culture chamber and that cultured in the second culture chamber are not limited to these cells, in the cell culturing method according to the present invention.

Further, an example of the cell culturing method according to the present invention includes a cell culturing method, in which a gel which serves as a cell scaffold material is housed in the first culture chamber, and in which the co-culture system having a tubular structure is caused to form a structured network on the gel.

Furthermore, an example of the cell culturing method according to the present invention includes a cell culturing method, in which a reagent is introduced into the second culture chamber in which the cell derived from the intestine is cultured, from the second introduction flow channel, and a metabolite of the cell derived from the intestine thus obtained is introduced into the first culture chamber via the first porous membrane and the first introduction flow channel.

In addition, an example of the cell culturing method according to the present invention includes a cell culturing method in which the culture medium discharged from the first culture chamber is dialyzed and is fed into the first culture chamber in a circulated manner. By this, an environment closer to in vivo can be realized.

The present invention is a technique for culturing cells, and for example, is a useful technique which is used for an artificial organ such as an artificial liver, or a drug metabolism test and the like.

The cell culturing device according to the present invention, for example, a second culture chamber which is connected via a first porous membrane to a halfway part of a flow channel (a first introduction flow channel) of a culture solution which is to be introduced into a first culture chamber in which a liver tissue is cultured. For example, a cell derived from an intestine is cultured in the second culture chamber and a drug to be tested is administered into the culture medium of the second culture chamber.

Figure 2:
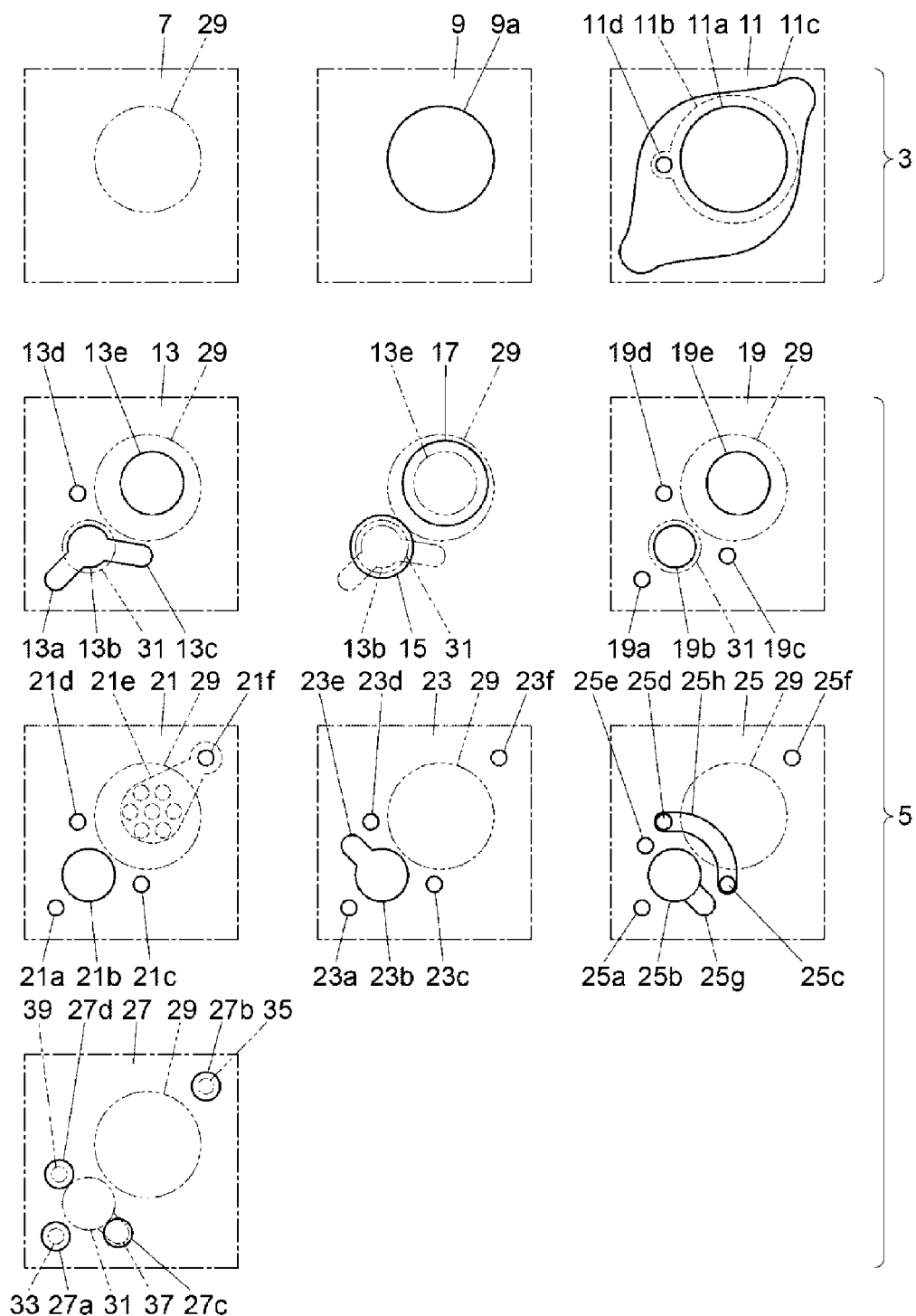
FIG. 2 is a plan view which shows the cell culturing device according to the same example by disassembling the cell culturing device.

FIG. 1 is a schematic plan view and a cross-sectional schematic diagram for illustrating an example of a cell culturing device. FIG. 2 is a plan view which shows the cell culturing device according to this example by disassembling the cell culturing device.

A cell culturing device 1 according to this example is roughly formed by a main body part 3 and a lid part 5. The main body part 3 is, for example, a part for culturing a liver tissue. The lid part 5 is, for example, a part for culturing an intestinal epithelial cell. The lid part 5 is detachable/attachable from/to the main body part 3.

The main body part 3 has a base plate 7, a PDMS block 9 and a PDMS block 11.

The base plate 7 of the main body part 3 is, for example, formed of synthetic quartz. Meanwhile, the base plate 7 is not limited to that having a plane shape. The base plate 7 may be anything as long as it is capable of being adsorbed by the PDMS block 9. For example, the base plate 7 may be a culture dish.

The PDMS block 9 and the PDMS block 11 are, for example, formed of SILPOT 184 (manufactured by Dow Corning Toray Co., Ltd.). The plane size of the PDMS blocks 9 and 11 is, for example, 25 mm×25 mm (millimeter). The thickness of the PDMS block 9 is, for example, 2.0 mm. The thickness of the PDMS block 11 for example, 1.0 mm.

The PDMS block 9 has a through hole 9a which has a diameter of, for example, 10 mm.

The PDMS block 11 has a through hole 11a, a recessed part 11b, a protruding part 11c and a through hole 11d.

The through hole 11a is formed at the position which is overlapped with the through hole 9a, when the PDMS block 9 and the PDMS block 11 are stuck together. The through hole 11a has, for example, a diameter of 10 mm.

The recessed part 11b is formed on the surface in contact with the PDMS block 9. The depth of the recessed part 11b is, for example, about 0.2 mm. The recessed part 11b has a peripheral part around the through hole 11a and a projected part protruding from the peripheral part. The width of the recessed part 11b at the peripheral part around through hole 11a is, for example, about 1.0 mm. With regard to the size of the projected part in the recessed part 11b, for example, the width is about 2.0 mm and the length is about 2.0 mm.

The protruding part 11c is formed in a convex shape bulging from the surface which is opposed to the surface in contact with the PDMS block 9. The height of the protruding part 11c is, for example, about 0.5 mm. The upper surface of the protruding part 11c constitutes the surface in contact with the lid part 5. The protruding part 11c is formed at the position which contains the position where the through hole 11a is formed. Meanwhile, the thickness of the PDMS block 11 is the thickness including the thickness of the protruding part 11c.

The through hole 11d is formed at the position which is overlapped with the projected part in the recessed part 11b. The diameter of the through hole 11d is, for example, 1.5 mm.

The forming process of the main body part 3 is briefly explained.

The PDMS block 11 in which the recessed part 11b and the protruding part 11c are formed is prepared. The recessed part 11b has a circular part having a diameter of about 12 mm and a projected part protruding from the circular part. The through hole 11d having a diameter of 1.5 mm is opened at the position which is overlapped with the projected part.

The PDMS block 11 in which the through hole 11a has not been formed and the PDMS block 9 in which the through hole 9a has net been formed are stuck together. At this time, it is preferable that the contact surfaces between the PDMS block 9 and the PDMS block 11 are subjected to an oxygen plasma treatment before being stuck together. The surface of the PDMS block 11 in contact with the PDMS block 9 is the surface on which the recessed part 11b is formed.

A through hole having a diameter of 10 mm and passing through the PDMS block 9 and 11 which are stuck together is formed so that the through hole is overlapped with the center of the circular part in the recessed part 11b. By this, the through hole 9a is formed in the PDMS block 9, and the through hole 11a is formed in the PDMS block 11.

The surface of the PDMS block 9 which is opposed to the PDMS block 11 and the base plate 7 are stuck together so that the main body part 3 is completed. At this time, it is preferable that the surface of the PDMS block 9 in contact with the base plate 7 is subjected to an oxygen plasma treatment. Meanwhile, it is also possible to stick the PDMS block 9 onto the base plate 7, a cell culture dish, and the like by utilizing the self-adsorption property of the PDMS block 9 though the oxygen plasma treatment is not performed.

Next, the lid part 5 is explained.

The lid part 5 has a silicone rubber sheet 13, a filter 15 (a first porous membrane), a filter 17 (a second porous membrane), a silicone rubber sheet 19, a PDMS block 21, a silicone rubber sheet 23, a PDMS block 25 and a PDMS block 27.

The plane size of the silicone rubber sheets 13, 19 and 23 as well as the PDMS blocks 21, 25 and 27 is, for example, 25 mm×25 mm.

The silicone rubber sheets 13, 19 and 23 are, for example, formed of a Silius extremely thin silicone rubber sheet (a product of Fuso Rubber Co., Ltd).

The PDMS blocks 21, 25 and 27 are, for example, formed of SILPOT 184 (manufactured by Dow Corning Toray Co., Ltd.).

The silicone rubber sheet 13 and the silicone rubber sheet 19 are provided in order hold the filters 15 and 17 by sandwiching the filters 15 and 17. The thickness of each of the silicone rubber sheets 13 and 19 is, for example, 0.1 mm.

The silicone rubber sheet 13 has a long hole 13a, a through hole 13b, a long hole 13c, a through hole 13d and a through hole 13e, which are, for example, formed by a method such as a punching method.

The width dimension of the long hole 13a is, for example, 2.0 mm. One end of the long hole 13a is connected to the through hole 13b.

The diameter of the through hole 13b is, for example, 4.0 mm.

The width dimension of the long hole 13c is, for example, 2.0 mm. One end of the long hole 13c is connected to the through hole 13b at a position different from the position where one end of the long hole 13a is connected to the through hole 13b. The other end of the long hole 13c is formed at the position which is overlapped with the through hole 11d in the PDMS block 11.

The through hole 13d is formed at the position which is overlapped with the through hole 11d in the main body part 3. The diameter of the through hole 13d is, for example, 1.5 mm.

The through hole 13e is formed at the position which is overlapped with a liver tissue culture chamber 29 in the main body part 3. The diameter of the through hole 13e is, for example, 5.0 mm.

The silicone rubber sheet 19 has through holes 19a, 19b, 19c and 19d, which are, for example, formed by a method such as a punching method.

The through hole 19a is formed at the position which is overlapped with the end part of the long hole 13a in the silicone rubber sheet 13. The diameter of the through hole 19a is for example, 1.5 mm.

The through hole 19b is formed at the position which is overlapped with the through hole 13b in the silicone rubber sheet 13. The diameter of the through hole 19b for example, 4.0 mm.

The through hole 19c is formed at the position which is overlapped with the end part of the long hole 13c in the silicone rubber sheet 13. The diameter of the through hole 19c is, for example, 1.5 mm.

The through hole 19d is formed at the position which is overlapped with the through hole 13d in the silicone rubber sheet 13. The diameter of the through hole 19d is for example, 1.5 mm.

A through hole the is formed at the position which is overlapped with the through hole 13e in the silicone rubber sheet 13. The diameter the through hole 19e is, for example, 5.0 mm.

The filter 15 is, for example, formed of a track-etched membrane PET with a pore size of 1 µm (a product of it4ip s.a.). The diameter of the filter 15 is, for example, 5 mm. The filter 15 is placed between the silicone rubber sheet 13 and the silicone rubber sheet 19 so that the filter 15 is overlapped with the through hole 13b and the through hole 19b.

The filter 17 is, for example, formed of a track-etched membrane PC with a pore size of 5 µm (a product of it4 ip s.a.). The diameter of the filter 17 is, for example, 6 mm. The filter 17 is placed between the silicone rubber 13 and the silicone rubber sheet 19 so that the filter 17 is overlapped with the through hole 13e and the through hole 19e.

For example, after an oxygen plasma treatment is performed on the surfaces of the silicone rubber sheets 13 and 19 on which these sheets are to be stuck together, the silicone rubber sheets 13 and 19 are stuck together in a state where the two filters 15 and 17 are sandwiched by the silicone rubber sheets 13 and 19. The filter 15 constitutes, for example, a culture surface for an intestinal epithelial cell. The filter 17 constitutes a filter of a culture medium discharging part of the liver tissue culture chamber 29.

The thickness of the PDMS block 21 is, for example, 1.0 mm. The PDMS block 21 has through holes 21a, 21b, 21c and 21d, a well as a recessed groove 21e and a through hole 21f. For example, the recessed groove 21e is formed during the molding of the PDMS block 21. The through holes 21a, 21b, 21c, 21d and 21f are formed after the molding of the PDMS block 21.

The through hole 21a is formed at the position which is with the through hole 19c in the silicone rubber sheet 19. The diameter of the through hole 21a is for example, 1.5 mm.

The through hole 21a is formed at the position which is overlapped with the through hole 19b in the silicone rubber sheet 19. The diameter of the through hole 21a is, for example, 4.5 mm.

The through hole 21c is formed at the position which is overlapped with the through hole 19c in the silicone rubber sheet 19. The diameter of the through hole 21c is, for example, 1.5 mm.

The through hole 21d is formed at the position which is overlapped with the through hole 19d in the silicone rubber sheet 19. The diameter of the through hole 21d is, for example, 1.5 mm.

The recessed groove 21e is formed on the surface to which the silicone rubber sheet 19 is stuck. The depth of the recessed groove 21e is, for example, 0.2 mm. The recessed groove 21e is formed to be astride the position which is overlapped with both the liver tissue culture chamber 29 and the through hole 19e in the silicone rubber sheet 19 and the through hole not overlapped with the liver tissue culture chamber 29. The depth of the recessed groove 21e is, for example, 0.2 mm. A plurality of projections are formed in the position of the recessed groove 21e which is overlapped with the through hole 19e. These projections are provided in order to prevent the filter 17 from sticking to the bottom surface of the recessed groove 21e.

The through hole 21f is formed at the position which is overlapped with the recessed groove 21e but which is not overlapped with the liver tissue culture chamber 29. The diameter of the through hole 21f is, for example 1.5 mm.

The thickness of the silicone rubber sheet 23 is, for example, 0.2 mm. The silicone rubber sheet 23 has through holes 23a, 23b, 23c and 23d as well as a long hole 23e and a through hole 23f.

The through hole 23a is formed at the position which is overlapped with the through hold 21a in the PDMS block 21. The diameter of the through hole 23a is, for example, 1.5 mm.

The through hole 23b is formed at the position which is overlapped with the through hole 21b in the PDMS block 21. The diameter of the through hole 23b is, for example, 4.5 mm.

The through hole 23c is formed at the position which is overlapped with the through hole 21c in the PDMS block 21. The diameter of the through hole 23c is, for example, 1.5 mm.

The through hole 23d is formed at position which is overlapped with the through hole 21d in the PDMS block 21. The diameter of the through hole 23d is, for example, 1.5 mm.

The width dimension of the long hole 23e is, for example, 2.0 mm. One end of the long hole 23e is connected to the through hole 23b.

The through hole 23f is formed at the position which is overlapped with the through hole 21f in the PDMS block 21. The diameter of the through hole 23f is, for example, 1.5 mm.

The thickness of the PDMS block 25 is, for example, 1.0 mm. The PDMS block 25 has through holes 25a, 25b, 25c, 25d, 25e and 25f as well as recessed grooves 25g and 25h. For example, the recessed grooves 25g and 25h are formed during the molding of the PDMS block 25. The through holes 25a, 25b, 25c, 25d, 25e and 25f are formed after the molding of the PDMS block 25.

The through hole 25a is formed at the position which is overlapped with the through hole 23a in the silicone rubber sheet 23. The diameter of the through hole 25a is, for example, 1.5 mm.

The through hole 25b is formed at the position which is overlapped with the through hole 23b in the silicone rubber sheet 23. The diameter of the through hole 25b is, for example, 4.5 mm.

The through hole 25c is formed at the position which is overlapped with the through hole 23c in the silicone rubber sheet 23. The diameter of the through hole 25c is, for example, 1.5 mm.

The through hole 25d is formed at the position which is overlapped with the through hole 23d in the silicone rubber sheet 23. The diameter of the through 25d is, for example, 1.5 mm.

The through hole 25e is formed at the position which is overlapped with the through hole 23e in the silicone rubber sheet 23. The diameter of the through hole 25e is, for example, 1.5 mm.

The through hole 25f is formed at the position which is overlapped with the through hole 23f in the silicone rubber sheet 23. The diameter of the through hole 25f is, for example, 1.5 mm.

The recessed grooves 25g and 25h are formed on the surface which is opposed to the surface to which the silicone rubber sheet 23 is stuck (formed on the surface to which the PDMS block 27 is stuck). The depth of the recessed groove 25g is, for example, 0.6 mm. The width dimension of the recessed groove 25g is, for example, 2.0 mm. The depth of the recessed groove 25h is, for example, 0.2 mm. The width dimension of the recessed groove 25h is for example, 1.7 mm.

One end of the recessed groove 25g is connected to the through hole 25b.

One end of the recessed groove 25g is formed at the position which is overlapped with the penetration groove 25c. The other end of the recessed groove 25g is formed at the position which is overlapped with the penetration groove 25d.

The thickness of the PDMS block 27 is, for example, 1.0 mm. The PDMS block 27 has through holes 27a, 27b, 27c and 27d. For example the through holes 27a, 27b, 27c and 27d are formed after the molding of the PDMS block 27.

The through hole 27a is formed at the position which is overlapped with the through hole 25a in the PDMS block 25. The through hole 27b is formed at the position which is overlapped with the through hole 25f in the PDMS block 25. The through hole 27c is formed at the position which is overlapped with the tip part of the recessed groove 25g in the PDMS block. The through hole 27d is formed at the position which is overlapped with the through hole 25e in the PDMS block 25.

The diameter of the through holes 27a, 27b, 27c and 27d is, for example, 1.5 mm.

The forming process of the lid part 5 is briefly explained.

The PDMS block 25, in which the recessed grooves 25g and 25h are formed, is prepared. In addition, the silicone rubber sheet 23 in which the long hole 23e is formed is prepared. The silicone rubber sheet 23 is stuck to the surface of the PDMS block 25 which is opposed to the surface on which the recessed grooves 25g and 25h are formed. At this time, it is preferable that the surface of the PDMS block 25 to which the silicone rubber sheet 23 is stuck is subjected to an oxygen plasma treatment before being stuck.

The through hole 25e having a diameter of 1.5 mm is formed to the PDMS block 25 and the silicone rubber sheet 23 after the PDMS block 25 and the silicone rubber sheet 23 are stuck together.

The PDMS block 21 in which the recessed groove 21e is formed is prepared. The surface of the PDMS block 21 which opposed to the surface on which the recessed groove 21e is formed, and the surface of the silicone rubber sheet 23 which is opposed to the PDMS block 25 are stuck together. At this time, it is preferable that the surface of the PDMS block 21 to which the silicone rubber sheet 23 is stuck is subjected to an oxygen plasma treatment before being stuck.

The through holes 21a, 23a, and 25a, the through holes 21b, 23b, and 25b, the through holes 21c, 23c, and 25c, the through holes 21d, 23d, and 25d as well as the through holes 21f, 23f, and 25f are formed to the PDMS block 21, the silicone rubber sheet 23 and the PDMS block 25 after the PDMS block 21, the silicone rubber sheet 23, and the PDMS block 25 are stuck together. At this time, the diameter of the through holes 21b, 23b, and 25b is expanded to 5 mm. The diameter of the through holes 21a, 23a and 25a, the through holes 21c, 23c, and 25c, the through holes 21d, 23d, and 25d as well as the through holes 21f, 23f, and 25f is 1.5 mm.

The silicone rubber sheets 13 and 19, between which the two filters 15 and 17 are sandwiched, are prepared. To the PDMS block 21, the silicone rubber sheet 23 and the PDMS block 25 which are stuck together beforehand, the silicone rubber sheet 19 is stuck to the surface of the PDMS block 21 on which the recessed groove 21e is formed.

The PDMS block 27, in which the through holes 27a, 27b, 27c and 27d are formed, is prepared. To the silicone rubber sheet 13 and 19, the PDMS block 21, the silicone rubber sheet 23 and the PDMS block 25 which are stuck together beforehand, the PDMS block 27 is stuck to the silicone rubber sheet 13. By this, the lid part 5 is completed.

In the cell culturing device 1, the main 3 and the lid part 5 are joined by the self-adsorption property of, for example, the PDMS block 11 and the silicone rubber sheet 13. By this, the main body part 3 and the lid part 5 are stably fixed to each other, for example, without using a special fixing means such as a screw and an adhesive agent. In addition, the main body part 3 can be easily attached/detached to/from the lid part 5, as needed.

In the cell culturing device 1, the through holes 9a and 11a in the main body part 3 constitute the layer tissue culture chamber 29 (a first culture chamber). In addition, the through hole 13e in the silicone rubber sheet 13 of the lid part 5 constitutes a portion of the liver tissue culture chamber 29. The bottom surface of the liver tissue culture chamber 29 is constituted by the base plate 7. The upper surface of the liver tissue culture chamber 29 is constituted by the filter 17.

The through holes 19b, 21b, 23b, and 25b in the lid part 5 constitute an intestinal epithelial cell culture chamber 31 (a second culture chamber). The lower surface of the intestinal epithelial cell culture chamber 31 is constituted by the filter 15. The upper surface of the intestinal epithelial cell culture chamber 31 to constituted by the PDMS block 27.

The through holes 27a, 25a, 23a, and 21a the long hole 13a, the through hole 13b, the long hole 13c, the through holes 19c, 21c, 23c, and 25c, the recessed groove 25h, the through holes 25d, 23d, 21d, 19d, and 13d in the lid part 5 constitute a culture medium feeding part 33 (a first introduction flow channel). In addition, the through hole 11d and the recessed part 11b in the main body part 3 also constitute a portion of the culture medium feeding path 33. The end port of the through hole 27a is a culture medium introducing port 33a.

The through hole 19e, a recessed groove 21b as well as the through holes 21f, 25f, and 27b in the lid part 5 constitute a culture medium discharging path 35 (a first discharge flow channel). The end part of the through hole 27b is a culture medium discharging port 35a.

The through holes 27c and 25i well as the recessed groove 25g in the lid part 5 constitute a reagent introducing path 37 (second introduction flow channel). The end part of the through hole 27c is a reagent introducing port 37a.

The through holes 27d and 25e as well as the long hole 23e in the lid part 5 constitute a reagent discharging path 39 (a second discharge flow channel). The end part of the through hole 27d is a reagent discharging port 39a.

The depth of the recessed groove 25g constituting the reagent introducing path 37 is, for example, 0.6 mm. In addition, the depth of the long hole 23e constituting the reagent discharging path 39, which corresponds to the thickness of the silicone rubber sheet 23 is, for example, 0.2 mm. The reason why the height of the flow channel of the reagent introducing path 37 is larger than the height of the flow channel of the reagent discharging path 39 is to make it easy to introduce cells into the intestinal epithelial cell culture chamber 31.

In addition, in the culture medium feeding path 33, for example, each of the part of the long hole 13c, the through holes 19c, 21c, 23c, and 25c and the part at the through holes 25d, 23d, 21d, 19d, and 13d constitutes a liquid collecting part 41, respectively. The liquid collecting part 41 is provided between the liver tissue culture chamber 29 and the intestinal epithelial cell culture chamber 31 in the culture medium feeding path 33.

The PDMS block 27 which constitutes the upper wall surface of the liquid collecting part 41 is an elastic member which is capable of being penetrated by a suction implement having a sharp tip, in which the through hole is capable of being closed when the suction implement is withdrawn after the penetration due to the elasticity of the member. A liquid, for example, a culture medium is collected from the liquid collecting part 41, as needed.

Meanwhile, though the liquid collecting parts 41 are provided in two spots in this example, the liquid collecting part 41 may be provided in one spot. Further, it is possible to use a part of the recessed groove 25h as a liquid collecting part.

In the cell culturing device 1, the main body part 3 in which a liver tissue is cultured can be attached/detached to/from the lid part 5 in which an intestinal epithelial cell is cultured.

A cell derived from an intestine, for example, an intestinal epithelial cell (here, Caco2) is introduced together with a culture medium into the intestinal epithelial cell culture chamber 31 in the lid part 5 from a reagent introducing port 39a. The intestinal epithelial cells are cultured under such a condition that a tight junction is formed on the filter 15. For example, the intestinal epithelial cells are cultured only in the lid part 5 in a state where the main body part 3 and the lid part 5 are separated from each other.

An example of a method for culturing a liver tissue is explained. A gel is introduced as a scaffold into the liver tissue culture chamber 29, for example, in a state where the main body part 3 is cooled. This gel is, for example, an EHS-gel. The EHS-gel is a preparation of basement membranes isolated from EHS mouse sarcoma cells, and is rich in laminins, collagen type IV and proteoglycans. The EHS-gel liquefies at a low temperature, and solidifies at a normal temperature. Accordingly, the EHS-gel can be solidified on the bottom surface of the liver tissue culture chamber 29 by pouring the EHS-gel into the liver tissue culture chamber 29 in a state where the cell culturing device 1 is cooled, and then leaving the EHS-gel to stand, for example, in an incubator at 37° C. or at room temperature.

An endothelial cell (for example, GH7) is seeded on the gel. A network of the endothelial cells is formed on the gel. A hepatic parenchymal cell is seeded on the network of the endothelial cells. In the liver tissue culture chamber 29, a co-culture system which contains a cell of the endothelial cell lineage and a cell of the hepatocyte lineage is co-cultured on the gel so that the co-culture system has a tubular structure. Examples of the cell of the endothelial cell lineage include, for example, a sinusoidal endothelial cell, a human umbilical vein (artery) endothelial cell TD2, GH7, and the like. Examples of the cell of the hepatocyte lineage include, for example, a hepatic parenchymal cell, HepaRG, Huh-7, Hep G2, TLR2, Hepa 1-6, a liver progenitor cell, and the like. Meanwhile, a cell which is different from a cell of the endothelial cell lineage and a cell of the hepatocyte lineage may be contained in the co-culture system which contains the cell of the endothelial cell lineage and the cell of the hepatocyte lineage.

It is confirmed that the intestinal epithelial cells are sufficiently proliferated in the intestinal epithelial cell culture chamber 31 of the lid part 5 and that the tight junction is formed. The main body part 3 in which the liver tissue is cultured in the liver tissue culture chamber 29 and lid part 5 in which the intestinal epithelial cell are cultured in the intestinal epithelial cell culture chamber 31 are stuck together. The joining surfaces of the warn body part 3 and the lid part 5 are both formed of a silicon rubber-based material. Accordingly, the liquid tightness between the main body part 3 and the lid part 5 can be maintained by using a simple jig which is capable of maintaining an appropriate pressure in a state where the main body part 3 and the lid part 5 are stuck together.

Further, the protruding part 11c having a convex shape is formed on the surface of the PDMS block 11 in the main body part 3 which is in contact with the lid part 5. The upper surface of the protruding part 11c and the silicone rubber sheet 13 in the lid part 5 are joined together. The plane size of the contact surface between the main body part 3 and the lid part 5 is smaller than the plane size of the cell culturing device 1. Owing to this structure, the contact between the main body part 3 and the lid part 5 at the outer circumferential part of the cell culturing device 1 which is irrelevant to liquid delivery and culture can be eliminated, and a force distribution to an unnecessary part can be suppressed and therefore, an effect of preventing liquid leakage is exhibited.

The culture medium is fed to the culture medium introducing port 33a, for example, by a syringe pump and the like. The fed culture medium flows into the liver tissue culture chamber 29 via the culture medium feeding path 33 which passes under the filter 15 of the intestinal epithelial cell culture chamber 31 in which intestinal epithelial cells are cultured. This culture medium is discharged from the culture medium discharging 35a via the filter 17 and the culture medium discharging path 35.

A culture medium or a reagent can be fed into the intestinal epithelial cell culture chamber 31 from the reagent introducing port 37a via the reagent introducing path 37. The culture medium and reagent are discharged from the reagent discharging port 39a after passing through the intestinal epithelial cell culture chamber 31 via the reagent discharging path 39. When a reagent is fed into the intestinal epithelial cell culture chamber 31, a metabolite is passed through the filter 15 at the surface of culture and is supplied to the culture medium feeding path 33 which is connected to the liver tissue culture chamber 29, after the reagent is absorbed by intestinal epithelial cells. Accordingly, it is important that the intestinal epithelial cells are densely cultured on the filter 15 while forming a tight junction.

The metabolite of the drug which is supplied to the culture medium feeding path 33 reaches a liver tissue which is cultured in the liver tissue culture chamber 29 via the culture medium feeding path 33 and the liquid collecting part 41. This structure makes it possible to simulate a mechanism by which the drug incorporated from the intestinal wall reaches the liver, and also makes it possible to evaluate pharmacokinetics in a state close to in vivo.

As described above, the cell culturing device 1 makes it possible to culture two types of cells and to introduce a metabolite of one type of cells into the other type of cells.

In addition, in the cell culturing device 1, the main body part 3 in which the liver tissue culture chamber 29 is formed can be attached/detached to/from the lid part 5 in which the intestinal epithelial cell culture chamber 31 is formed. Therefore, the main body part 3 and the lid part 5 can be combined together at a good timing after culturing each of a liver tissue and an intestinal epithelial cell under an appropriate condition, respectively, in a state where the main body part 3 and the lid part 5 are separated. Accordingly, the cell culturing device 1 enables efficient measurement.

Figure 3:
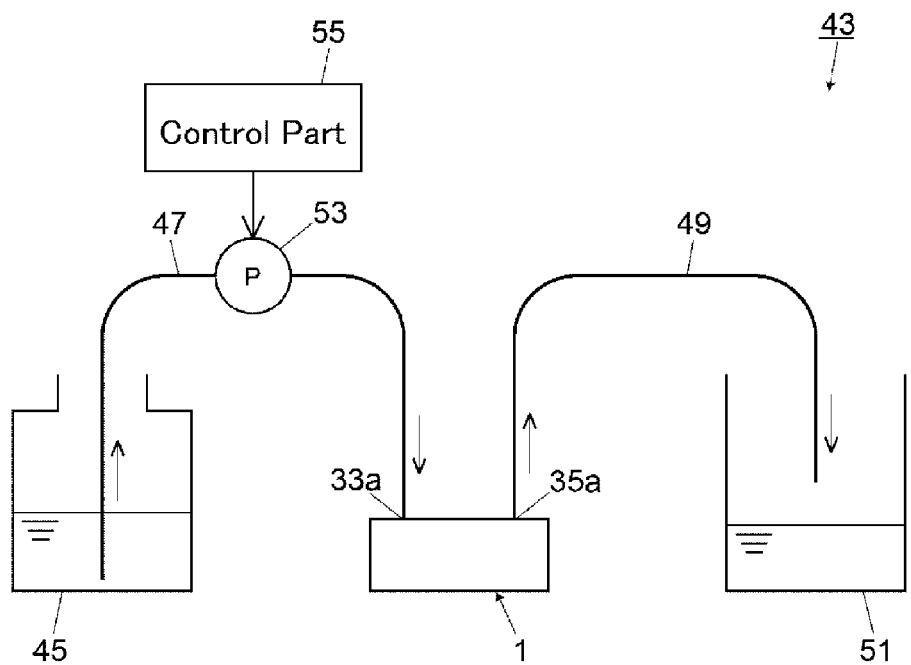
FIG. 3 is a schematic diagram for illustrating an example of a cell culturing system.

FIG. 3 is a schematic diagram for illustrating an example of a cell culturing system which uses the cell culturing device 1 according to the present example.

A cell culturing system 43 is a combination of the cell culturing device 1 and a culture medium feeding part which feeds the culture medium into the cell culturing device 1. The culture medium feeding part has a culture medium housing part 45, a culture medium feeding pipe 47, a culture medium discharging pipe 49, a waste liquid housing part 51, a liquid feeding pump 53, and a control part 55.

One end of the culture medium feeding pipe 47 is inserted into the culture medium housing part 45. The other end of the culture medium feeding pipe 47 is connected to the culture medium introducing port 33a of the cell culturing device 1. One end of the culture medium discharging pipe 49 is connected to the culture medium discharging port 35a of the cell culturing device 1. The other end of the culture medium discharging pipe 49 is inserted into the waste liquid housing part 51. The liquid feeding pump 53 is connected to the culture medium feeding pipe 47. The control part 55 controls the operation of the liquid feeding pump 53.

The culture medium housed in the culture medium housing part 45 is sucked by the liquid feeding pump 53, and is sent to the cell culturing device 1 from the culture medium introducing port 33a through the culture medium feeding pipe 47. The culture medium supplied to the cell culturing device 1 from the culture medium introducing port 33a is introduced into the liver tissue culture chamber 29 from the peripheral surface of the liver tissue culture chamber 29 by passing through the culture medium feeding path 33. (See FIG. 1).

In accordance with the introduction of the culture medium into the liver tissue culture chamber 29, a part of the culture medium within the liver tissue culture chamber 29 is discharged from the liver tissue culture chamber 29 to the outside from the culture medium discharging port 35a through the filter 17 and the culture medium discharging path 35. The culture medium discharged from the culture medium discharging port 35a is discharged to the waste liquid housing part 51 through the culture medium discharging pipe 49.

When the culture medium within the liver tissue culture chamber 29 is discharged from culture medium discharging path 3, the cell culturing device 1 makes the culture medium pass through the filter 17, and therefore, it is possible to reduce probability of clogging of the culture medium discharging path 35 due to the gel which is peeled off and the like.

The cell culturing system 43 is capable of stabilizing environments surrounding cells, tissues, and the like by feeding the culture medium little by little in a manner similar to in vivo. Accordingly, a stable culture of a cell can be realized. As described above, the cell culturing device 1 and the cell culturing system 43 are advantageous for culturing a cell for a long period of time.

In addition, when a reagent is supplied into the intestinal epithelial cell culture chamber 31, a metabolite is supplied to the culture medium feeding path 33 which is connected to the liver tissue culture chamber 29 by passing through the filter 15 on the culture surface, after the reagent is absorbed by the intestinal epithelial cells. The metabolite which is supplied to the culture medium feeding path 33 is supplied into the liver tissue culture chamber 29, together with the culture medium. Accordingly, the cell culturing device 1 and the cell culturing system 43 make it possible to conduct a test on a reagent in an environment similar to an environment found in vivo.

Further, the cell culturing device 1 makes it possible to collect the metabolite which is supplied from the intestinal epithelial cell culture chamber 31 to the culture medium feeding path 33, together with the culture medium, at the liquid collecting part 41 (see FIG. 1). This collection of the metabolite is, for example, performed by making a suction implement having a sharp tip penetrate the PDMS block 27 which constitutes the upper wall surface of the liquid collecting part 41 in such a way that the suction implement having the sharp tip is inserted into the liquid collecting part 41, and sucking the metabolite and the culture medium. When the suction implement is withdrawn from the PDMS block 27, the through hole formed by the penetration of the suction implement is closed by the elastic force of the PDMS block 27. Accordingly, it is possible to continue supplying the culture medium and the like to the liver tissue culture chamber 29, even after the metabolite and the like are collected at the liquid collecting part 41.

In the cell culturing system 43 shown in FIG. 3, the liquid feeding pump 53 is provided with the culture medium feeding pipe 47, which has a function which continuously feeds the culture medium into the liver tissue culture chamber 23, but the cell culturing system according to the present invention is not limited thereto.

Figure 4:
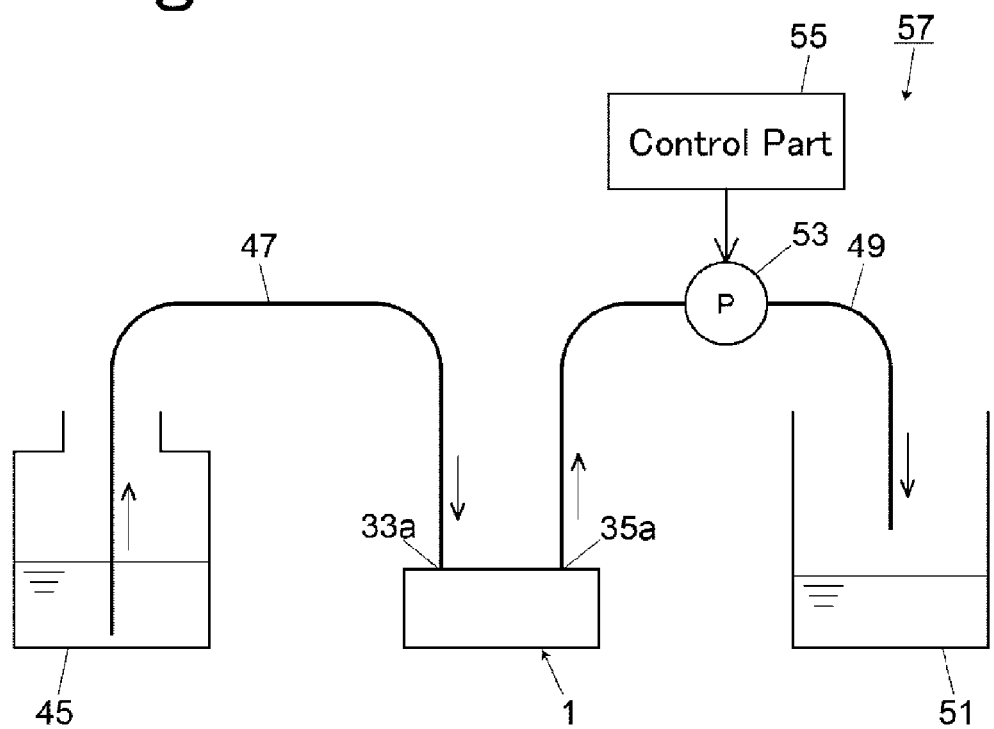
FIG. 4 is a schematic diagram for illustrating another example of a cell culturing system.

As an example, as shown in FIG. 4, a cell culturing system 57, which is an example of the present invention, may be a system in which the culture medium discharging pipe 49 is provided with the liquid feeding pump 53, which has a function which continuously sucks the culture medium from the inside of the liver tissue culture chamber 29. Meanwhile, the cell culturing system according to the present invention is not limited to the constitution shown in FIG. 3 or FIG. 4.

The present invention is capable of stabilizing environments surrounding cells, tissues, and the like by feeding the culture medium little by little in a manner similar to in vivo. Accordingly, the present invention is capable of realizing a stable culture of cells.

Incidentally, a body fluid circulates in vivo, while being the dialyzed by the kidneys. In that sense, the above-described cell culturing systems 43 and 57 cannot evaluate an effect such as an accumulation of a trace amount of an expression product.

Accordingly, by adding a function of dialysis to a hallway part of the cell culturing system according to the present invention, which gives a system in which a culture medium circulates, it is possible to realize an evaluation system closer to an actual living body.

According to the present invention, for example, when conducting a pharmacokinetic study, the liver function evaluation considering an influence of an absorption in an intestine is possible, and therefore, a test closer to that conducted in a living body can be realized. In addition, the cell culturing system according to the present invention is a system which utilizes a fluid control technology, and it is possible, for example, to develop a system which considers effects of a dialysis at the kidneys, and further, to develop an integrated system which also considers influences by other organs.

Figure 5:
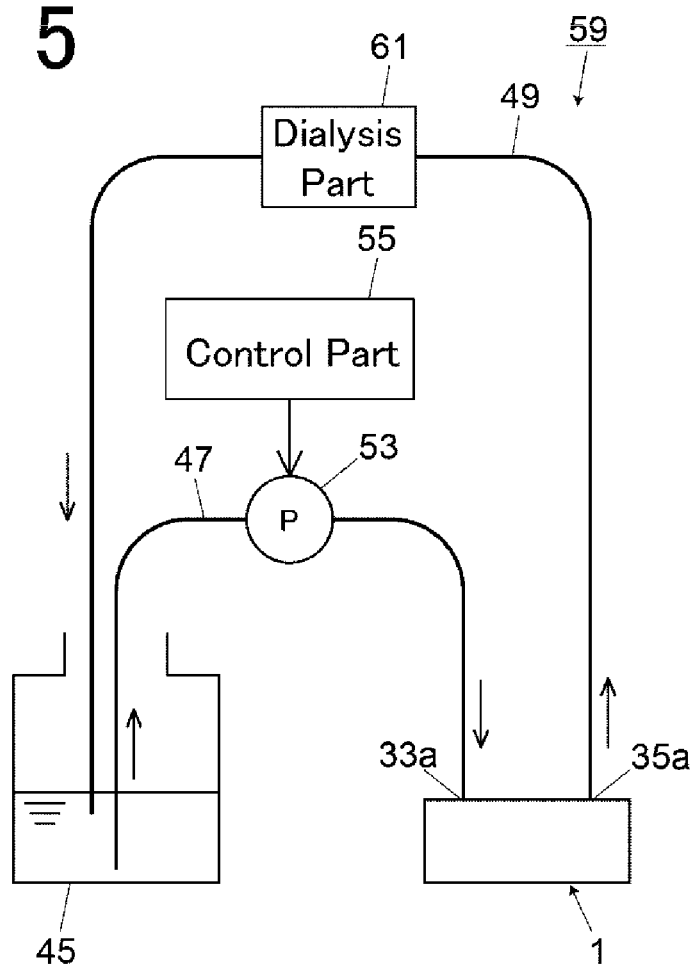
FIG. 5 is a schematic diagram for illustrating a further example of a cell culturing system.

FIG. 5 is a schematic diagram for illustrating a further example at a cell culturing system which utilizes the cell culturing device 1 according to the present example. In FIG. 5, to the parts which exhibit similar functions to those shown in FIG. 3 and FIG. 4, the same reference signs are given.

A culture medium feeding part of a cell culturing system 59 feeds a culture medium into the liver tissue culture chamber 29 of the cell culturing device 1 in a circulated manner. The culture medium feeding part has the culture medium housing part 45, the culture medium feeding pipe 47, the culture medium discharging pipe 49, the liquid feeding pump 53, the control part 55, and a dialysis part 61.

One end of the culture medium discharging pipe 49 is connected to the culture medium discharging port 35a of the cell culturing device 1. The other end of the culture medium charging pipe 49 is connected to the culture medium housing part 45. The dialysis part 61 is provided in a halfway part of the culture medium discharging pipe 49. The dialysis part 61 is, for example, a small-sized dialyzer. The dialysis part 61 has a function which filtrates the circulated culture medium such that unnecessary substances are removed.

The cell culturing system 59 sucks up the culture medium from the culture medium housing part 45 in which the culture medium is housed, for example, by the liquid feeding pump 53 such as a syringe pump, and supplies the culture medium to the cell culturing device 1, and thereafter, puts the culture medium back into the original culture medium housing pact 45 via the dialysis part 61. By this, the cell culturing system 59 is capable of evaluating reagent and the like under an environment closer to that in an actual living body.

Figure 6:
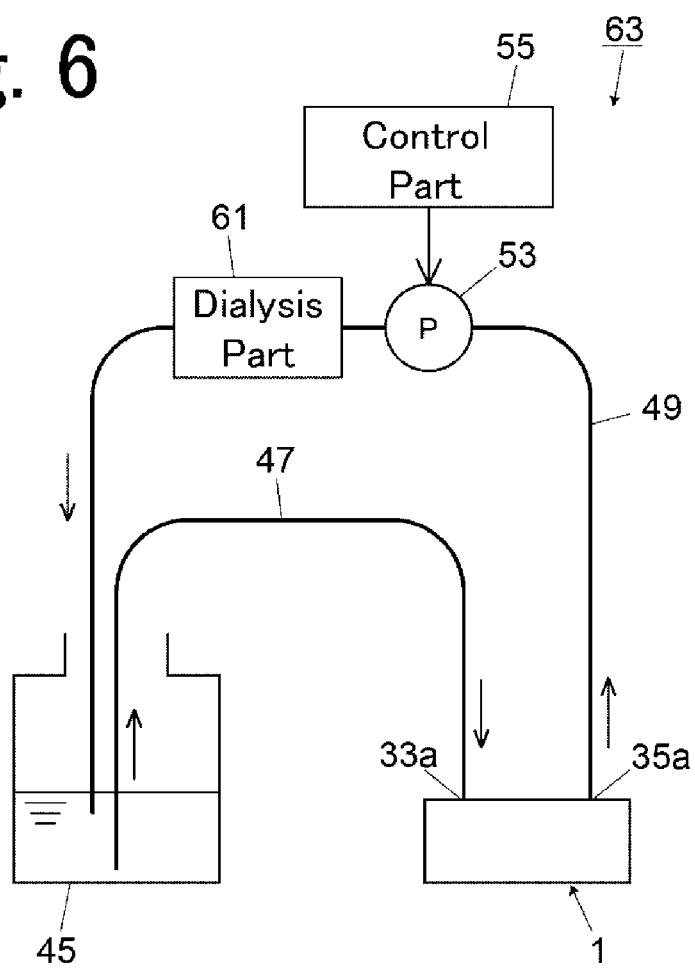
FIG. 6 is a schematic diagram for illustrating a further example of a cell culturing system.

FIG. 6 is a schematic diagram for illustrating a further example of a cell culturing system which uses the cell culturing device 1, according to the present example. In FIG. 6, to the parts which exhibit similar functions to those in FIG. 5, the same reference signs are given.

A cell culturing system 63, which is an example of the present invention, is different from the cell culturing system 59 shown in FIG. 5 in the connecting position of the liquid feeding pump 53. In the cell culturing system 63, the liquid feeding pump 53 is connected to the culture medium discharging pipe 49 at position between the cell culturing device 1 and the dialysis part 61. Meanwhile, the liquid feeding pump 53 may be connected to the culture medium discharging pipe 49 at a position between the dialysis part 61 and the culture medium housing part 45.

Figure 7:
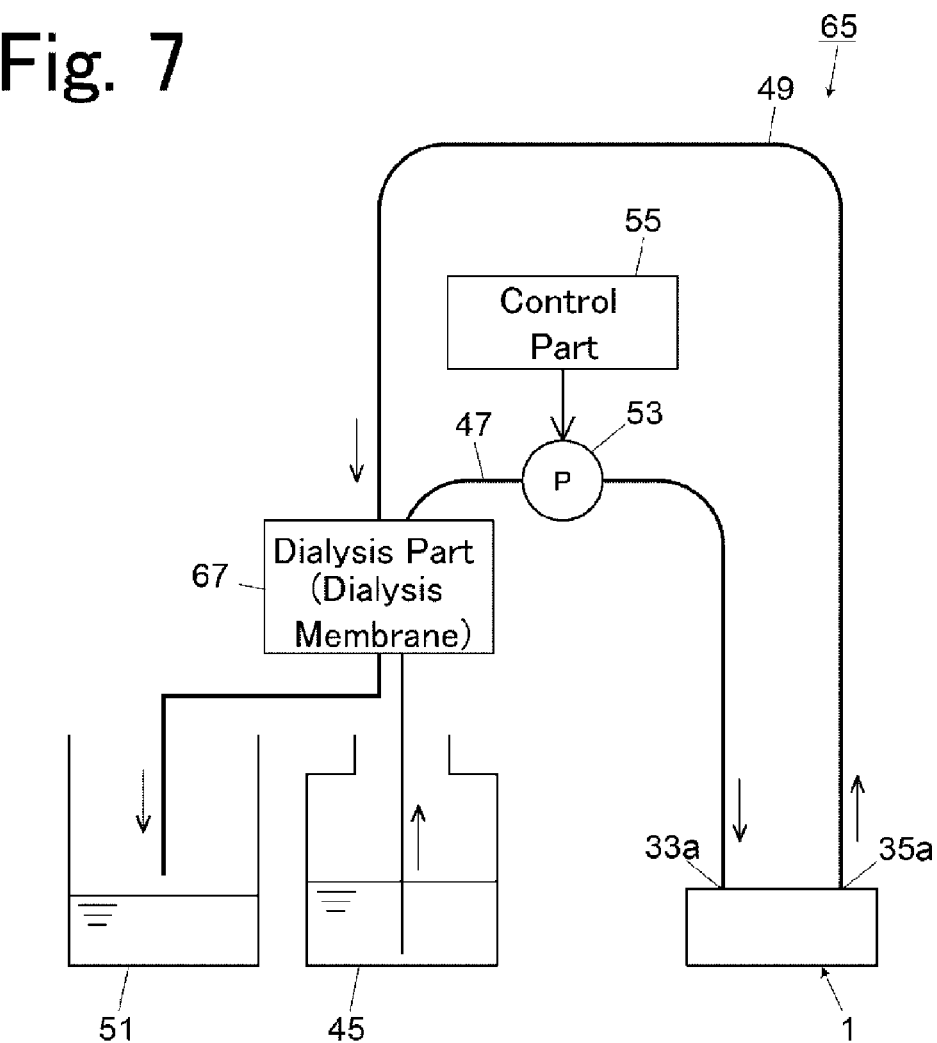
FIG. 7 is a schematic diagram for illustrating a further example of a cell culturing system.

FIG. 7 is a schematic diagram for further example of a cell culturing system which uses the cell culturing device 1 according to the present example. In FIG. 7 to the parts which exhibit similar functions to those shown in FIG. 3, the same reference signs are given.

A cell culturing system 63, which is an example of the present invention, further has a dialysis part 67 compared to the cell culturing system 43 shown in FIG. 3. The dialysis part 67 is constituted by a dialysis membrane which is provided between two flow channels of the culture medium feeding pipe 47 and of the culture medium discharging pipe 49. This dialysis membrane is formed or, for example, a Spectra Series (a product of Spectrum, Inc.).

The cell culturing device 1, which is an example of the present invention, is capable of culturing a cell in the liver tissue culture chamber 29 by supplying a culture medium at a flow rate, for example, of about 40 μL/h (microliter/hour), and therefore, the cell culturing device 1 requires, a small amount of the culture medium. Accordingly, the cell culturing system 65, which is an example of the present invention, is also capable of using a dialysis membrane as the dialysis part 67.

Meanwhile, the cell culturing system 65 may feed a dialysate instead of the culture medium to the cell culturing device 1.

Figure 8:
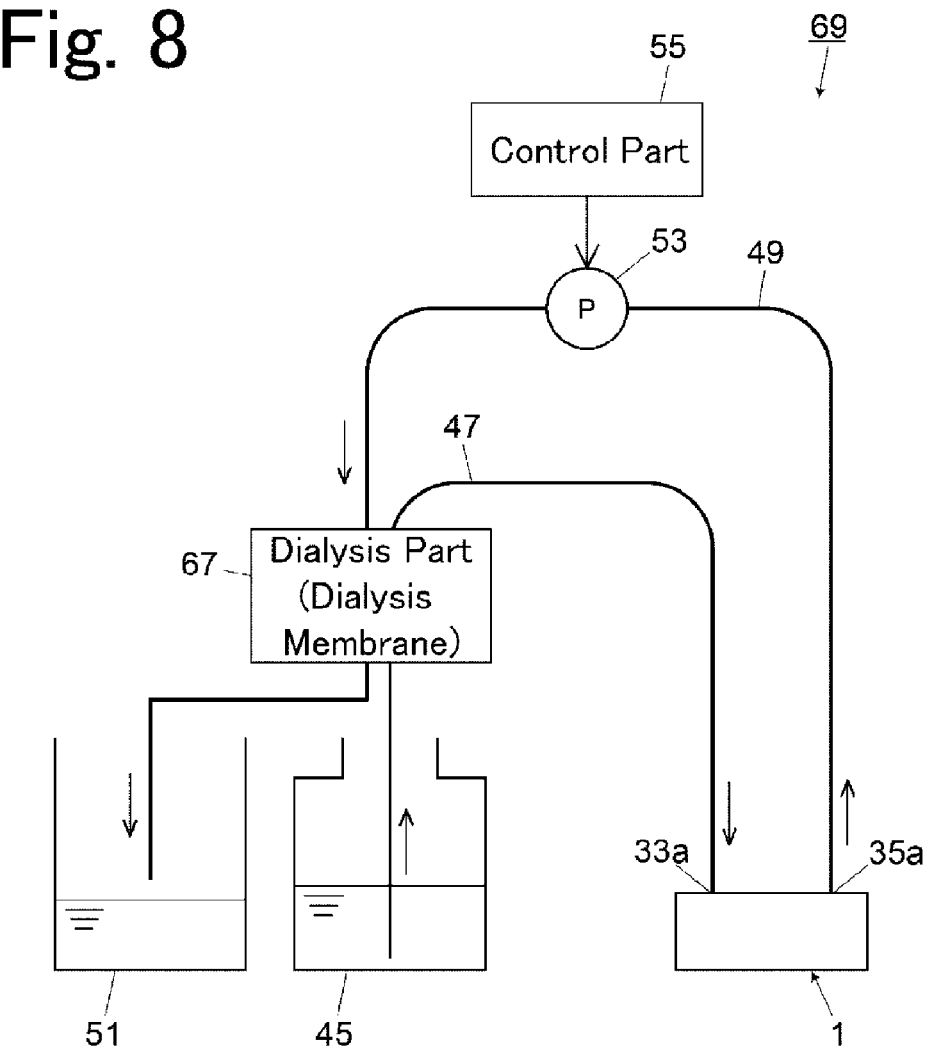
FIG. 8 is a schematic diagram for illustrating a further example of a cell culturing system.

In addition, the liquid feeding pump 53 may be connected to the culture medium discharging pipe 49 at a point between the cell culturing device 1 and the dialysis part 61, as in a cell culturing system 69, which is an example of the present invention shown in FIG. 8. Further, the liquid feeding pump 53 may be connected to the culture medium discharging pipe 49 at a point between the dialysis part 61 and the waste liquid housing part 51. Furthermore, the liquid feeding pump 53 may be connected to the culture medium feeding pipe 47 at a point between the culture medium housing part 45 and the dialysis part 61.

Incidentally, the cell culturing device 1 explained above has the liquid collecting part 41. In contrast, it is not necessary for the cell culturing device according to the present invention to have a liquid collecting part.

Figure 9:
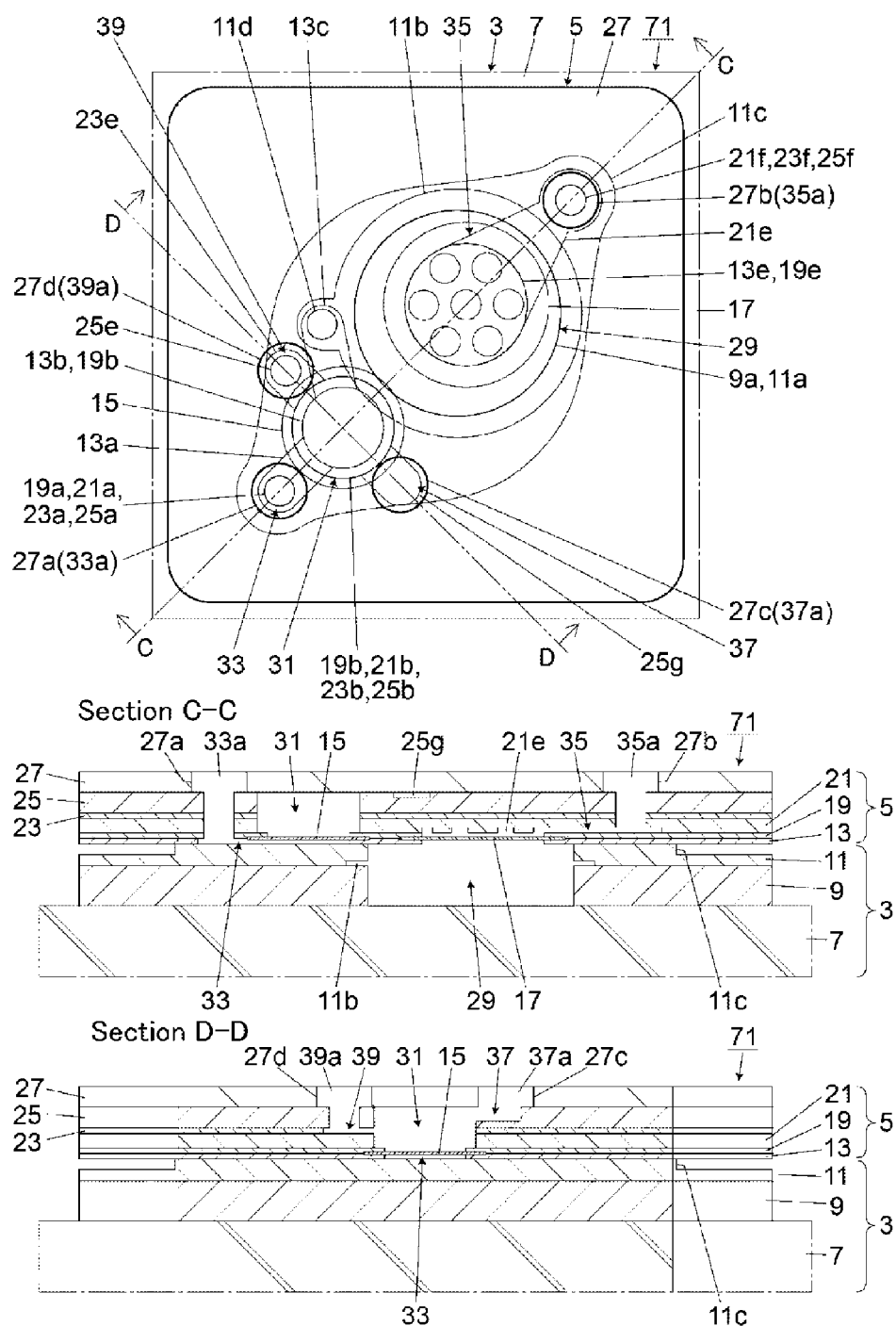
FIG. 9 is a schematic plan view and a cross-sectional schematic diagram for illustrating another example a cell culturing device.
Figure 10:
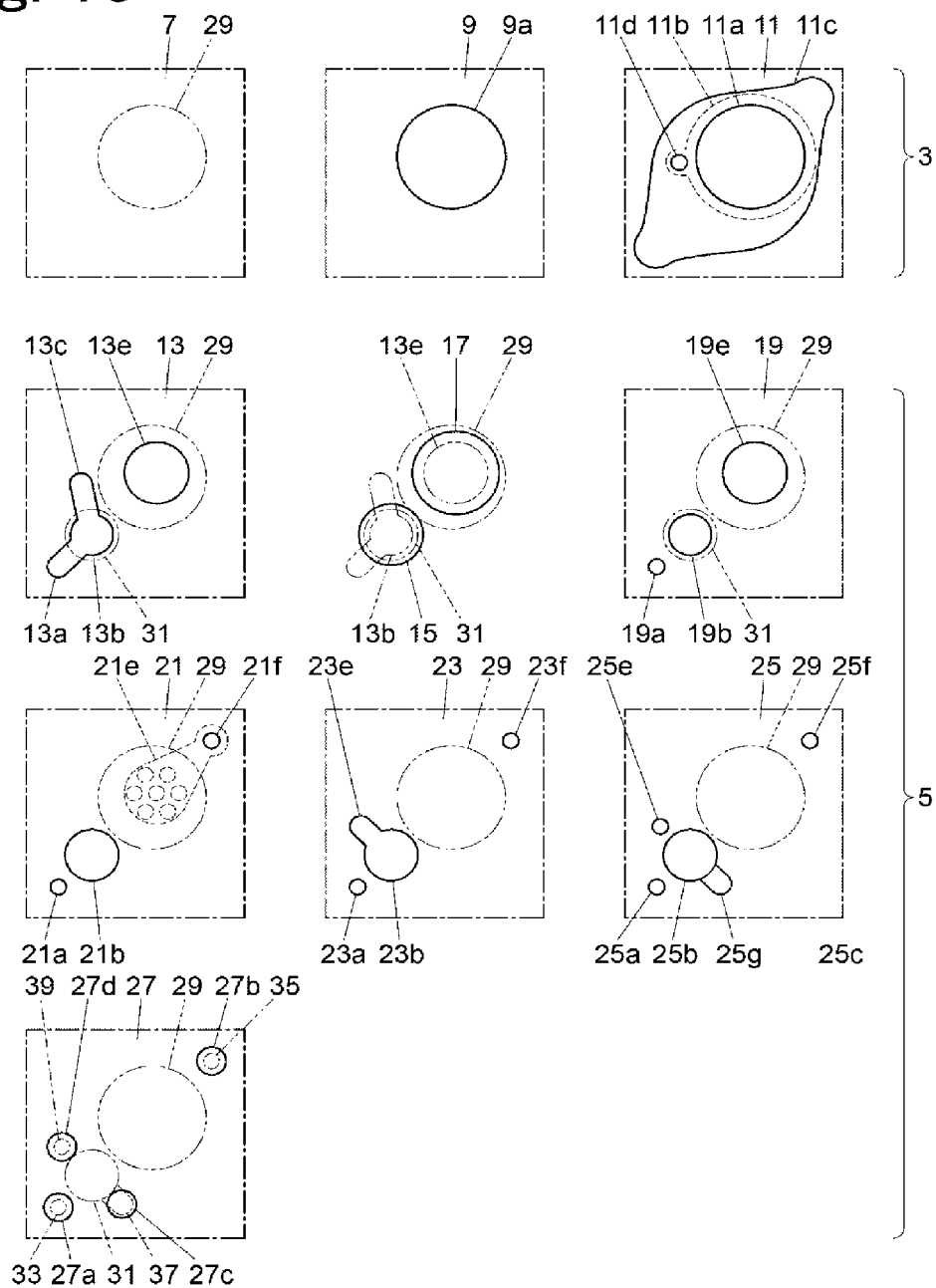
FIG. 10 is a plan view which shows the cell culturing device shown in FIG. 9 by disassembling the cell culturing device.

FIG. 9 is a schematic plan view and a cross-sectional schematic diagram for illustrating another example of a cell culturing device. FIG. 10 is a plan view which shows the cell culturing device of this example by disassembling the cell culturing device. In FIG. 9 and FIG. 10, to the parts which are the same as those shown in FIG. 1 and FIG. 2, the same reference signs are given.

A cell culturing device 71 of this example lacks the liquid collecting part 41 compared to the cell culturing device 1 which is explained by referring to FIG. 1 and FIG. 2. That is, the cell culturing device 71 lacks the through holes 19c, 21c, 23c and 25c as well as the through holes 13d, 19d, 21d, 23d and 25d (see FIG. 1 and FIG. 2). In addition, the cell culturing device 71 lacks the recessed groove 25h (see FIG. 1 and FIG. 2).

In the silicone rubber sheet 13 of the cell culturing device 71, the distal end part of the long hole 13c which is opposite to the through hole 13b is formed at the position which is overlapped with the through hole 11d in the PDMS block 11.

The culture medium feeding path 33 is formed by the through holes 27a, 25a, 23a, 21a and 19a, the long hole 13a, the through hole 13b, the long hole 13c, the through hole 11d as well as the recessed part 11b.

The cell culturing device 71 is capable of exhibiting the same actions and effects as those exhibited by the cell culturing device 1, which is explained by referring to FIG. 1 and FIG. 2, except for the effects of the liquid collecting part 41 (see FIG. 1 and FIG. 2).

In addition, the cell culturing system, which is explained by referring to, for example, FIG. 3 to FIG. 8, is capable of using the cell culturing device 71 instead of the cell culturing device 1.

The examples of the present invention are explained above, but the constitutions, arrangements, numerical values, and the like in the examples are only given as examples, and the present invention is nor limited thereto. Various modifications are possible in the scope of the present invention which is described in claims.

As an example, in the above-described examples of the cell culturing device according to the present invention, the first culture chamber is the liver tissue culture chamber 29, and the second culture chamber is the intestinal epithelial cell culture chamber 31, but the first culture chamber and the second culture chamber are not limited thereto in the cell culturing device according to the present invention. Cell cultured in the first culture chamber and in the second culture chamber may be any of the various types of cells.

In addition, in the above-described examples of the cell culturing device, the culture medium discharging path 35 (the first discharge flow channel) is connected to the liver tissue culture chamber 29 (the first culture chamber) via the filter 17 (the second porous membrane). By this, for example, the clogging of the culture medium discharging path 35 due to the influx of a substance in the liver tissue culture chamber 29 such as a cell and a scaffold material (a gel) into the culture medium discharging path 35 can be prevented. However, it is not necessary to arrange the filter 17 (the second porous, membrane) in the cell culturing device according to the present invention.

Further, the cell culturing devices 1 and 71 of the above-described examples have the main body part 3 and the lid part 5 which is detachably attached to the main body part 3. Furthermore, the liver tissue culture chamber 29 the first culture chamber) is formed in the main body part 3, and has an opening on the surface of the main body part 3 which is in contact with the lid part 5. By this, for example, a substance such as a cell, a scaffold material and a culture medium can be placed in the liver tissue culture chamber 29 without interposing the culture medium feeding path 33 (the first introduction flow channel) and the culture medium discharging path 35 (the first discharge flaw channel), in a state where the main body part 3 and the lid part 5 are separated. However, the cell culturing device according to the present invention may have a structure which does not have the detachable main body part or the lid part.

In addition, in the cell culturing devices 1 and 71 of the above-described examples, the material of a contact surface between the main body part 3 and the lid part 5 is formed of a PDMS or a silicone rubber. By this, the lid part 5 can be stably fixed to the main body part 3 due to the self-adsorption property, for example, without using a special fixing means such as a screw and an adhesive agent. Further, the main body part 3 can be easily attached/detached to/from the lid part 5, as needed. However, the material of a contact surface between the main body part 3 and the lid part 5 is not limited to a PDMS or a silicone rubber, and materials ether than the PDMS and the silicone rubber may be employed.

Further, the cell culturing devices 1 and 71 of the above-described examples have the protruding part 11c which is provided by forming the surface of the main body part 3 in contact with the lid part 5 in a convex shape. By this, the plane size of the contact surface between the main body 3 and the lid part 5 is smaller than the plane size of the cell culturing devices 1 and 71. By making the plane size of the contact surface between the main body part 3 and the lid part 5 smaller, a force distribution to an unnecessary part can be suppressed. By this, the adherence between the main body part 3 and the lid part 5 an be improved. Meanwhile, the convex shape may be formed only on the surface of the lid part 5 in contact with the main body part 3, or the convex shape may be formed on both the surface of the Main body part 3 in contact with the lid part 5 and the surface of the lid part 5 in contact with the main body part 3. Furthermore, in the cell culturing device according to the present invention, both the surface of the main body part 3 in contact with the lid part 5 and the surface of the lid part 5 in contact with the main body part 3 may be flat surfaces.

In addition, in the cell culturing devices 1 and 71 of the above-described examples, the intestinal epithelial cell culture chamber 31 (the second culture chamber) is formed in the lid part 5. By this, cells can be cultured in the first culture chamber and in the second culture chamber, respectively, under conditions and environments different from each other, by separating the main body part in which the first culture chamber is formed and the lid part in which the second culture chamber is formed. However, the intestinal epithelial cell culture chamber 31 (the second culture chamber) may be formed in the main body part 3, or the intestinal epithelial cell culture chamber 31 (the second culture chamber) may also be formed to be astride the main body part 3 and the lid part 5, in the cell culturing device according to the present invention.

DESCRIPTION OF REFERENCE SIGNS

1: Cell culturing device
3: Main body part
5: Lid part
15: Filter (First porous membrane)
17: Filter (Second porous membrane)
29: Liver tissue culture chamber (First culture chamber)
31: Intestinal epithelial cell culture chamber (Second culture chamber)
33: Culture medium feeding path (First introduction flow channel)
35: Culture medium discharging path (First discharge flow channel)
37: Reagent introducing path (Second introduction flow channel)
39: Reagent discharging path (Second discharge flow channel)
41: Liquid collecting part
53: Liquid feeding pump
61: Dialysis part

The invention claimed is:
1. A cell culturing device, comprising:
a first culture chamber;
a first introduction flow channel connected directly to the first culture chamber, wherein one end of the first introduction flow channel is an introducing port;

a first discharge flow channel connected to the first culture chamber;

a second culture chamber which is connected directly to a halfway part of the first introduction flow channel via a first porous membrane, wherein said halfway part is between the introducing port and the first culture chamber; and a second introduction flow channel and a second discharge flow channel which are connected to the second culture chamber.

2. The cell culturing device according to claim 1, wherein the first discharge flow channel is connected to the first culture chamber via a second porous membrane.

3. The cell culturing device according to claim 1,
wherein the first introduction flow channel has a liquid collecting part between the first culture chamber and the second culture chamber, and wherein at least a part of the wall of the liquid collecting part is formed by an elastic member which is configured to be penetrated by a suction implement having a sharp tip, wherein the through hole is configured to be closed when the suction implement is withdrawn after the penetration due to the elasticity of the member.

4. The cell culturing device according to claim 1, which comprises a main body part and a lid part which is detachably attached to the main body part,
wherein the first culture chamber is formed in the main body part, and has an opening on the surface of the main body part which is in contact with the lid part.

5. The cell culturing device according to claim 4, wherein the material of a contact surface between the main body part and the lid part is a PDMS or a silicone rubber.

6. The cell culturing device according to claim 4,
wherein at least one of the surface of the main body part in contact with the lid part and the surface of the lid part in contact with the main body part is formed in a convex shape, and wherein the plane size of the contact surface between the main body part and the lid part is smaller than the plane size of said device.

7. The cell culturing device according to claim 4, wherein the second culture chamber is formed in the lid part.

8. The cell culturing device according to claim 1,
wherein a co-culture system containing at least an endothelial cell and a hepatic parenchymal cell is co-cultured in the first culture chamber,
and wherein a cell derived from an intestine is cultured in the second culture chamber.

9. The cell culturing device according to claim 8,
wherein a gel which serves as a cell scaffold material is housed in the first culture chamber,
and wherein the co-culture system having a tubular structure forms a structured network on the gel.

10. A cell culturing system, comprising:
the cell culturing device according to claim 1, and
a culture medium feeding part which feeds a culture medium into the first culture chamber by connecting a pump to the cell culturing device.

11. The cell culturing system according to claim 10,
wherein the culture medium feeding part feeds the culture medium to the first culture chamber by circulating the culture medium,
and wherein the cell culturing system further comprises a dialysis part in a halfway part of the culture medium circulating line of the culture medium feeding part.

12. A cell culturing method, comprising the following steps in the following order:
culturing cells in the first culture chamber and in the second culture chamber, respectively, by using the cell culturing device according to claim 1, and
introducing a liquid in the second culture chamber into the first culture chamber via the first porous membrane and the first introduction flow channel.

13. The cell culturing method according to claim 12,
wherein cells are cultured in the main body part of the first culture chamber and in the second culture chamber which is formed in the lid part, respectively, in a state where the main body part and the lid part are separated from each other, by using the a cell culturing device wherein the second culture chamber is formed in the lid part, and thereafter, the main body part and the lid part are joined together.

14. The cell culturing method according to claim 12,
wherein a co-culture system containing at least an endothelial cell and a hepatic parenchymal cell is co-cultured in the first culture chamber,
and wherein a cell derived from an intestine is cultured in the second culture chamber.

15. The cell culturing method according to claim 14,
wherein a gel which serves as a cell scaffold material is housed in the first culture chamber,
and wherein the co-culture system having a tubular structure is caused to form a structured network on the gel.

16. The cell culturing method according to claim 14,
wherein a reagent is introduced into the second culture chamber, in which the cell derived from the intestine is cultured, from the second introduction flow channel, and a metabolite of the cell derived from the intestine thus obtained is introduced into the first culture chamber via the first porous membrane and the first introduction flow channel.

17. The cell culturing method according to claim 14, wherein the culture medium discharged from the first culture chamber is dialyzed and is fed into the first culture chamber in a circulated manner.

* * * * *